United States Patent
Liu et al.

(10) Patent No.: US 12,225,639 B2
(45) Date of Patent: Feb. 11, 2025

(54) AEROSOL GENERATING DEVICE WITH REMOVABLE CHAMBER

(71) Applicant: JT International S.A., Geneva (CH)

(72) Inventors: Pingkun Liu, Guangdong (CN); Yongbao Yuan, Guangdong (CN); Juan José Moreno Rodríguez, Geneva (CH); Damian Dickson, Weybridge (GB)

(73) Assignee: JT International S.A. (CH)

( * ) Notice: Subject to any disclaimer, the term of this patent is extended or adjusted under 35 U.S.C. 154(b) by 677 days.

(21) Appl. No.: 15/734,321

(22) PCT Filed: Jun. 20, 2019

(86) PCT No.: PCT/EP2019/066401
§ 371 (c)(1),
(2) Date: Dec. 2, 2020

(87) PCT Pub. No.: WO2019/243540
PCT Pub. Date: Dec. 26, 2019

(65) Prior Publication Data
US 2021/0219615 A1   Jul. 22, 2021

(30) Foreign Application Priority Data

Jun. 20, 2018 (EP) .................................... 18178688
Oct. 3, 2018 (EP) .................................... 18198485

(51) Int. Cl.
*H05B 3/42* (2006.01)
*A24F 7/00* (2006.01)
(Continued)

(52) U.S. Cl.
CPC ................. *H05B 3/42* (2013.01); *A24F 7/00* (2013.01); *A24F 7/02* (2013.01); *A24F 40/42* (2020.01);
(Continued)

(58) Field of Classification Search
CPC ... H05B 3/42; H05B 6/02; H05B 6/10; H05B 6/101; A24F 7/00; A24F 7/02;
(Continued)

(56) References Cited

U.S. PATENT DOCUMENTS

2011/0290269 A1   12/2011   Shimizu
2015/0013696 A1   1/2015   Plojoux et al.
(Continued)

FOREIGN PATENT DOCUMENTS

CN   106028850 A   10/2016
CN   106418699 A   2/2017
(Continued)

OTHER PUBLICATIONS

International Search Report for Application No. PCT/EP2019/066401 mailed Aug. 12, 2019, 3 pages.
(Continued)

*Primary Examiner* — Justin M Kratt
(74) *Attorney, Agent, or Firm* — Lerner David LLP (57) ABSTRACT

A portable aerosol-generating device for receiving an aerosol-generating substance includes a chamber arranged to receive an aerosol-generating substance and an aerosol-generating unit configured to generate an aerosol from the aerosol-generating substance for a user to inhale in use. The chamber is configured to be releasably inserted into the device through an opening in the device. This allows the chamber to be removed from the device and cleaned between consecutive uses of the device.

14 Claims, 6 Drawing Sheets

(51) Int. Cl.
*A24F 7/02* (2006.01)
*A24F 40/42* (2020.01)
*A24F 40/465* (2020.01)
*A24F 40/85* (2020.01)
*A61M 11/04* (2006.01)
*A61M 15/00* (2006.01)
*A61M 15/06* (2006.01)
*A24F 40/10* (2020.01)
*A24F 40/20* (2020.01)
*A24F 40/40* (2020.01)
*H05B 6/02* (2006.01)
*H05B 6/10* (2006.01)

(52) U.S. Cl.
CPC ............ *A24F 40/465* (2020.01); *A24F 40/85* (2020.01); *A61M 11/042* (2014.02); *A61M 15/0021* (2014.02); *A61M 15/06* (2013.01); *A24F 40/10* (2020.01); *A24F 40/20* (2020.01); *A24F 40/40* (2020.01); *A61M 11/04* (2013.01); *A61M 11/041* (2013.01); *H05B 6/02* (2013.01); *H05B 6/10* (2013.01); *H05B 6/101* (2013.01)

(58) Field of Classification Search
CPC ........ A24F 40/42; A24F 40/465; A24F 40/85; A24F 40/10; A24F 40/20; A24F 40/40; A61M 11/042; A61M 15/0021; A61M 15/06; A61M 11/04; A61M 11/041
See application file for complete search history.

(56) References Cited

U.S. PATENT DOCUMENTS

| | | | |
|---|---|---|---|
| 2015/0216234 A1* | 8/2015 | Chung | A24F 40/485 131/329 |
| 2017/0000190 A1 | 1/2017 | Wu | |
| 2017/0042251 A1 | 2/2017 | Yamada et al. | |
| 2017/0143042 A1 | 5/2017 | Batista et al. | |
| 2017/0156403 A1* | 6/2017 | Gill | B65D 43/02 |
| 2017/0172215 A1 | 6/2017 | Li et al. | |
| 2018/0049472 A1 | 2/2018 | Mahler et al. | |
| 2018/0116277 A1 | 5/2018 | Besso | |

FOREIGN PATENT DOCUMENTS

| | | |
|---|---|---|
| CN | 106535680 A | 3/2017 |
| CN | 107095344 A | 8/2017 |
| CN | 107205494 A | 9/2017 |
| CN | 107529814 A | 1/2018 |
| CN | 207011682 U | 2/2018 |
| CN | 207054784 U | 3/2018 |
| CN | 207151933 U | 3/2018 |
| CN | 108354230 A | 8/2018 |
| EP | 3167728 A1 | 5/2017 |
| GB | 2527597 A | 12/2015 |
| JP | 2014-533513 A | 12/2014 |
| JP | 2017-163974 A | 9/2017 |
| JP | 2017526381 A | 9/2017 |
| JP | 2017-192393 A | 10/2017 |
| JP | 2018-504134 A | 2/2018 |
| KR | 20170110566 A | 10/2017 |
| WO | 2010/090338 A1 | 8/2010 |
| WO | 2013076098 A2 | 5/2013 |
| WO | 2015198015 A1 | 12/2015 |
| WO | 2016124550 A1 | 8/2016 |
| WO | 2016135271 A1 | 9/2016 |
| WO | 2017115184 A1 | 7/2017 |
| WO | 2017/194763 A2 | 11/2017 |
| WO | 2017/194769 A1 | 11/2017 |
| WO | 2017220274 A1 | 12/2017 |
| WO | 2018019543 A1 | 2/2018 |
| WO | 2018/050610 A1 | 3/2018 |
| WO | 2018/120206 A1 | 7/2018 |

OTHER PUBLICATIONS

International Search Report for PCT/EP2019/076843 mailed Jan. 30, 2020; 4 pages.
Search Report dated May 5, 2022 from Office Action for Chinese Application No. 201980040740.9 issued May 11, 2022. 3 pgs.

* cited by examiner

AEROSOL GENERATING DEVICE WITH REMOVABLE CHAMBER

CROSS-REFERENCE TO RELATED APPLICATIONS

The present application is a national phase entry under 35 U.S.C. § 371 of International Application No. PCT/EP2019/066401, filed Jun. 20, 2019, published in English, which claims priority to European Application No. 18178688.0 filed Jun. 20, 2018, and European Application No. 18198485.7 filed Oct. 3, 2018, the disclosures of which are incorporated herein by reference.

BACKGROUND

The present invention relates to an aerosol-generating device with a removable chamber.

Devices which heat, rather than burn, a substance to produce a vapour for inhalation have become popular with consumers in recent years.

Many hand-held vaporisers comprise a chamber surrounded by a heating mechanism and connected to a mouthpiece. A vapour-generating substance is placed inside the chamber and the heating mechanism causes a vapour to be generated which can be inhaled by the user through the mouthpiece.

There are many different flavours and types of vapour-generating substance for users to choose from, depending on the desired flavour and inhalation experience. Most vaporisers are compatible with these different flavours and styles of substances so that one vaporiser may be used with a variety of different vapour-generating substances.

However, vaporisers are typically hard to clean and maintain properly. Thus, repeated use of the same vaporiser with different flavours of substance can lead to flavours from a previous substance bleeding into the flavours of a subsequent substance due to lingering flavour present in the chamber and other internal components of the vaporiser. Thus, overtime stale vapour begins to build up within the vaporiser and the quality of the user's experience decreases.

In addition, dust and dirt may build up within the vaporiser through repeated inhalation of air through the vaporiser. Thus, over time, the vaporiser becomes unhygienic to use.

It would be desirable to provide a hand-held vaporiser which can be properly cleaned and maintained between uses.

The present invention seeks to overcome at least some of the above problems.

SUMMARY OF INVENTION

According to an aspect of the present invention there is provided a portable aerosol generating device for receiving an aerosol-generating substance, the device comprising a chamber configured to receive an aerosol-generating substance and an aerosol-generating unit configured to generate an aerosol from the aerosol-generating substance for a user to inhale in use, wherein the chamber is configured to be releasably inserted into the device through an opening in the device.

Thus, the chamber may be releasably attached to the aerosol-generating device. This may allow a user to remove the chamber from the aerosol-generating device so that the chamber can be cleaned after use.

The opening may be arranged in the aerosol-generating unit. The chamber may be configured to be releasably inserted into the aerosol-generating unit through the opening in the aerosol-generating unit. This may provide a device with a simple structure as the chamber can be inserted directly into and removed from the aerosol-generating unit, where the aerosol is generated, rather than into another part of the device which does not generate the aerosol and which would therefore require a more complicated structure.

The opening may be configured to be closed, preferably, releasably sealed. This may ensure that once the aerosol-generating substance has been received by the chamber, the aerosol-generating substance is sealed from the surrounding environment. This may help preserve the aerosol-generating substance and ensure that the quality of the aerosol generated from the aerosol-generating substance is not compromised. In addition, sealing the chamber may prevent the aerosol-generating substance from becoming dislodged or from falling out of the chamber.

The opening may be configured to be closed, preferably, releasably sealed by a cover. The cover may provide a straight forward means of sealing the opening, keeping the structure of the device simple. The cover may therefore be in an open position or a closed position.

The cover may comprise a lid. The cover may comprise a cap. The cover may comprise any other suitable device which is capable of releasably sealing, or closing, an opening.

The opening may be releasably sealed by the cover using a releasable sealing means. The releasable sealing means may comprise a slide mechanism. For example, the cover may cooperate with the aerosol-generating device so that the cover may be slid away from the opening, along a surface of the aerosol-generating device to expose the chamber. To re-seal the chamber, the cover may be slid towards to the opening, along the same, or a different, surface of the aerosol-generating device.

The releasable sealing means may comprise a pivot joint. For example, the cover may be attached to the aerosol-generating device using a pin and the cover may be configured to rotate about the pin, in the plane of the cover, to open and close the opening. The releasable sealing means may comprise a hinge joint. The releasable sealing means may comprise any other suitable mechanism for allowing a cover to releasably seal an opening.

The cover may remain attached to the aerosol-generating device in both the sealed and the unsealed configurations. This may reduce the likelihood of the user misplacing the cover when they are accessing the chamber, for example during cleaning or when filling the chamber with aerosol-generating substance.

In other embodiments, the cover may be attached to the device when in the sealed configuration but unattached from the device when in the unsealed configuration. Thus, the cover may be releasably attached to the aerosol-generating device. This may provide the user with unhindered access to the chamber making it easier for the user to fill the chamber with the aerosol-generating substance. Additionally, by completely removing the cover from the opening, the chamber may be removed more easily from the aerosol-generating device as there will be a low risk of parts of the sealing mechanism getting in the way of the path of the chamber into and out of the aerosol-generating device. Thus, a detachable cover may facilitate easy insertion and removal of the chamber from the device.

The cover may be releasably attached to the aerosol-generating device using a releasable attachment means. The releasable attachment means may comprise a screw mechanism. The releasable attachment means may comprise a push-fit mechanism. The releasable attachment means may comprise a snap-fit mechanism. The releasable attachment means may comprise any other suitable mechanism for releasably attaching the cover to the aerosol-generating device.

The cover may comprise an air inlet. The cover may comprise a plurality of air inlets. The plurality of air inlets may be regularly spaced apart from each other. The air inlets may allow air to be drawn into the aerosol-generating device during usage. The user is therefore able to drawn air into the device, when the cover is in a closed position, which can be turned into an aerosol and then inhaled by the user.

The air inlet may be located within the body of the aerosol-generating unit. In this case, the air inlets may be located between the cover and the chamber. The air inlets may be provided in the form of grooves. The grooves may extend away from the centre of the aerosol-generating unit towards an external surface of the aerosol-generating unit. The grooves may allow air to be drawn into the device when the cover is in the closed position.

The chamber may remain in fluid communication with the atmosphere when the cover is in the closed position. This allows air to be drawn into the chamber without the cover being open.

The chamber may be configured to receive the aerosol-generating substance through the opening in the aerosol-generating device. This may allow the user to quickly and easily fill the chamber with an aerosol-generating substance when needed.

The chamber may be arranged substantially opposite the mouthpiece, along a longitudinal axis of the aerosol-generating device. That is, the chamber may be at a first end of the device and the mouth piece may be at a second end of the device. Having the components of the aerosol-generating device in line with each other may reduce the complexity of the aerosol-generating device and help ensure correct alignment of the components.

The aerosol-generating unit may comprise a heater. The heater may be configured to substantially surround walls of the chamber. The heater may be an induction heater or a resistive heater. The heater may heat up the aerosol-generating substance contained within the chamber so that an aerosol is generated. The chamber may therefore be thought of as an oven which can be removed from the device.

In other examples the device may comprise an induction heater having an electromagnetic inductor surrounding or positioned next to the chamber. The induction heater provides the device with a means of transferring heat to the aerosol-generating substance within the chamber such that the aerosol-generating substance is heated and vapour is produced for inhalation.

Whilst the aerosol generating substance will typically produce a gas or a solid and/or liquid suspension in gas when heated, it will be appreciated that the terms 'vapour' and 'aerosol' are used interchangeably here, and refer generally to the substance which is produced when the aerosol generated substance is heated.

The electromagnetic inductor being positioned next to or surrounding the chamber allows for heating a large proportion of the aerosol-generating substance, facilitating a uniform constant heating and thus aiding in maintaining a controlled temperature in the chamber. Advantageously, having an electromagnetic inductor surrounding or being positioned next to the chamber provides the generation of an efficient electromagnetic field through the chamber. Thus, in this case, the device comprises an induction heating assembly configured to heat the chamber, and the aerosol-generating substance contained within the chamber, in order to generate an aerosol. The use of induction heating via an induction heating assembly, instead of using resistive heating, allows the structure of the aerosol-generating device to remain simple and/or the aerosol-generating substance to be heated efficiently, compared to a device having a resistive heating assembly.

In examples where the device comprises an electromagnetic inductor, the chamber may further comprise a susceptor. The susceptor absorbs electromagnetic energy from the electromagnetic inductor and converts the absorbed energy to heat. In the case of the aerosol generating device comprising an electromagnetic inductor the chamber may further comprise susceptor material such that the electromagnetic inductor heats the susceptor material in use. The susceptor material may comprise one or more, but not limited, of aluminium, iron, nickel, stainless steel and alloys thereof, e.g. nickel chromium.

The chamber may be substantially cylindrical in shape. Preferably, where the chamber acts as a susceptor in an induction heated embodiment, the chamber has a resonant frequency which lies in the Kilohertz range (preferably between about 10 Khz and about 500 Khz, most preferably between 100 KHz and 500 Khz) and preferably the electromagnetic inductor is a driving solenoid having associated control electronics to automatically drive the solenoid at a frequency at or close to the resonant frequency of the chamber (or the resonant frequency of the combined susceptor load and driving solenoid, where the combined susceptor load may include one or more additional susceptor elements contained within the chamber) in order to maximise the efficiency of the heating based on the electrical power required to drive the solenoid.

The chamber may have an open end and a closed end. The open end of the chamber may be substantially opposite the closed end of the chamber. The chamber may be configured to be inserted into the aerosol-generating unit such that the open end of the chamber coincides with the opening of the aerosol-generating device. This allows the user to fill the chamber with an aerosol-generating substance without having to remove the chamber from the aerosol-generating unit. Thus, the same opening can be used to insert the chamber in the device and to fill the chamber with an aerosol-generating substance.

The chamber may comprise an opening. The opening may be positioned within the closed end of the chamber. Thus, the opening may be substantially opposite the open end of the chamber. The opening may have a width, or diameter, that is less than the width, or diameter, of the chamber. The opening may have a width, or diameter, that is less than that of the open end of the chamber. The opening in the chamber may allow the generated aerosol to leave the chamber.

The aerosol-generating device may comprise a mouthpiece. The chamber may be in fluid communication with the mouthpiece. Thus, the aerosol-generating unit may comprise a fluid passage which connects the chamber and the mouthpiece together. The fluid passageway may be connected to the chamber at the opening of the chamber. This allows the aerosol generated in the chamber to be inhaled by the user at the mouthpiece.

The mouthpiece may comprise an air outlet. The air outlet may be in fluid communication with the chamber via the fluid passage. The air outlet may provide a convenient and comfortable means for the user to inhale the aerosol from the device through the mouthpiece.

The chamber may be connected to the mouthpiece via a fluid passageway. Thus, the fluid passageway provides the fluid communication between the chamber and the mouthpiece. The fluid passageway may be substantially aligned with the longitudinal axis of the aerosol-generating device. This configuration may help keep the construction of the device simple.

The fluid passageway may comprise a fluid tube. The fluid tube may connect the chamber to the mouthpiece. The fluid tube may allow aerosol generated by the aerosol-generating unit to flow from the chamber to the air outlet in the mouthpiece.

The fluid tube may be at least the same length as the length of the fluid passageway. The fluid tube may have a length that is greater than the length of the fluid passageway. This allows a user to remove the heating chamber from the device by pushing the end of the fluid tube which protrudes from the fluid passageway. The user therefore does not have to come into contact with the heating chamber in order to remove the heating chamber. Furthermore, having a tube with a length greater than that of the passageway may help ensure that the aerosol is completely transferred from the chamber into the mouthpiece.

The fluid tube may be configured to be releasably inserted into the fluid passageway. Thus the fluid tube may be removable. The fluid tube may be inserted and removed through the opening in the aerosol-generating device. The chamber and the fluid tube may be inserted and removed from the device using the same opening, which may help keep the structure of the aerosol-generating device simple. Being able to remove the tube from the aerosol-generating device may allow the user to clean the tube when the device is not being used. A clean fluid tube may help preserve the taste and flavour of the aerosol generated from the aerosol-generating substance.

There may be a snug, or tight, fit between the external surface of the fluid tube and the internal surface of the fluid passageway. Thus, the fluid tube may be held in place in the fluid passageway through friction. This ensures that the fluid tube will not become dislodged during use. A friction fit will also ensure that the tube does not become dislodged if the chamber has been removed.

The aerosol-generating unit may comprise a sealing means to seal between the fluid tube and the fluid passageway. The sealing means may also seal between the opening in the chamber and the fluid passageway. The sealing means may prevent aerosol from leaking out from the chamber and/or the fluid tube into the aerosol-generating unit and aerosol-generating device. Thus, the sealing means may ensure that the aerosol-generating unit is fluid tight. This may help prevent damage to other parts of the aerosol-generating unit which are not designed to come into contact with the aerosol. This may help extend the useful lifetime of the aerosol-generating device.

The sealing means may comprise an O-ring. The sealing means may comprise any other suitable device capable of sealing against fluid. The aerosol-generating device may comprise a plurality of sealing means. There may be a sealing means provided at each end of the fluid tube in the fluid passageway. Thus, both ends of the fluid passageway may be fluid tight.

The mouthpiece may be configured to be releasably detached from the aerosol-generating unit. Thus, the mouthpiece may comprise a releasable detachment means. The releasable detachment means may comprise a screw mechanism. Once the mouthpiece is detached from the aerosol-generating unit, a part of the fluid tube may be exposed. The exposed part of the fluid tube may be used to release the chamber from the aerosol-generating unit. Thus, the chamber may be configured to be removed from the aerosol-generating device using the fluid tube to dislodge the chamber through the opening in the aerosol-generating device.

The fluid tube may be fixed to the device.

In some embodiments, the chamber and the fluid tube are integrally formed. That is, the chamber and the fluid tube form a single component. In other embodiments the chamber and fluid tube are fixedly attached to each other. The chamber and fluid tube may therefore be inserted into and removed from the aerosol-generating device together. This makes assembly and disassembly of the device easier as the user has fewer components to remove and re-construct. Advantageously, fewer components and a simple construction provides a device that is easier for the user to clean.

By providing a single chamber and fluid tube component, an airtight connection between the chamber, the fluid tube, and the fluid passageway is achieved. Advantageously, a single component avoids the need for the user to ensure two separate components are sealed correctly when assembling the device. A single component therefore ensures there is no air gap between the chamber and fluid passageway.

In some embodiments the fluid passageway, and/or the fluid tube, may comprise a low heat conductive material whose heat conductivity is less than a conductivity of a material from which the chamber is made. The low heat conductive material may be a high temperature proof plastic. The material from which the chamber is made may comprise metal such as stainless. By providing a fluid passageway, and/or fluid tube, and chamber comprising materials having different thermal conductivities, a thermal break is introduced between the fluid passageway, or fluid tube, and the chamber. The thermal break prevents heat from the chamber travelling up the fluid passageway. This helps the aerosol generated in the chamber from the aerosol-generating substance get cool enough in a short amount of time. Quickly cooling the aerosol ensures that the aerosol reaches an appropriate temperature to be inhaled by the user by the time the aerosol reaches the mouthpiece.

According to another aspect of the present invention there is provided a method of removing a chamber from an aerosol-generating device the method comprising the steps of providing an aerosol-generating device comprising an opening and releasably inserting the chamber into the aerosol-generating device through the opening in the device, wherein the chamber is configured to receive an aerosol-generating substance.

BRIEF DESCRIPTION OF FIGURES

Embodiments of the present invention will now be described, by way of example only, with reference to the accompanying figures, in which.

DETAILED DESCRIPTION

Figure 1:
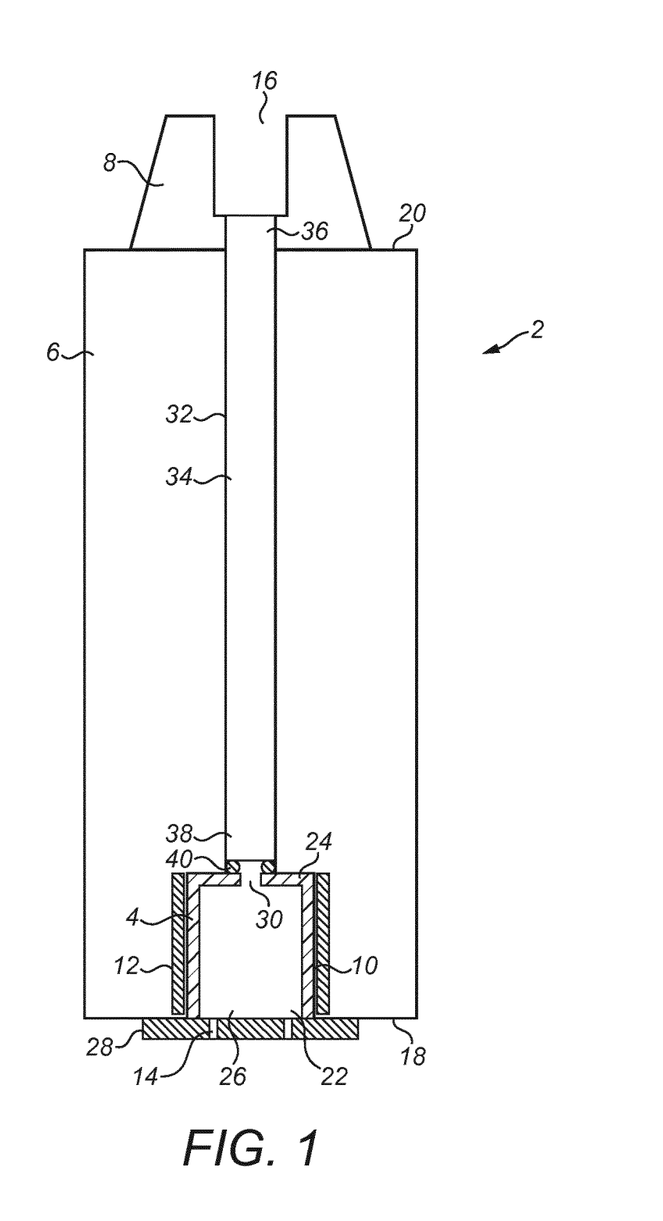
FIG. 1 is a schematic view of an aerosol-generating device comprising a removable chamber.
Figure 2:
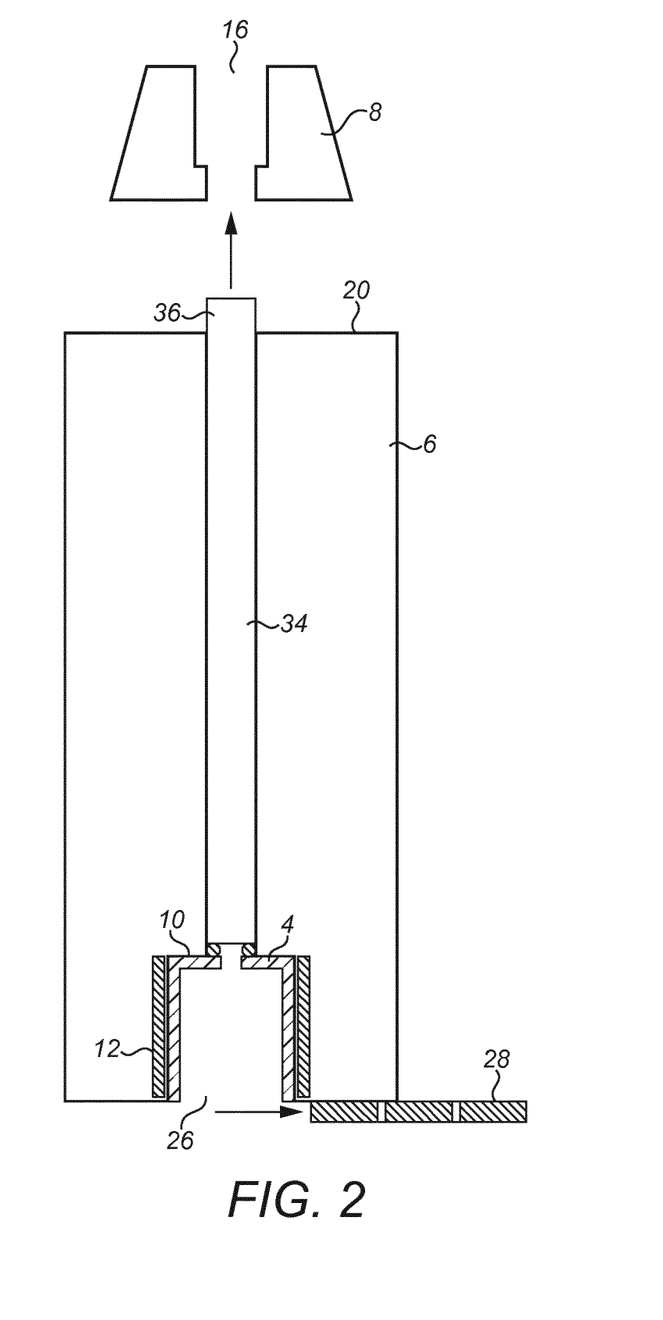
FIG. 2 is a schematic view of an aerosol-generating device comprising a removable chamber.

A portable aerosol-generating device 2 according to the invention is shown generally in FIG. 1. The aerosol-generating device 2 is a hand-held device, by which we mean that the device is able to be held and supported by a user un-aided in a single hand. The device 2 includes a chamber 4 for receiving an aerosol-generating substance, an aerosol-generating unit 6 for generating an aerosol from the aerosol-generating substance, and a mouthpiece 8. The aerosol-generating unit 6 heats the aerosol-generating substance inside the chamber 4, generating an aerosol. The aerosol is then able to be inhaled by a user at the mouthpiece 8. The aerosol-generating substance may include at least one of tobacco, humectant, glycerine, and propylene glycol. However, any other volatile substance could be used from which a vapour or aerosol can be generated.

The user inhales the aerosol by drawing air into the device 2, through the chamber 4 containing the aerosol-generating substance, and out of the mouthpiece 8 when the chamber 4 is heated. Heating is achieved by the chamber 4 being located in a heating portion 10 of the aerosol-generating unit 6 surrounded by a heating element, or heater, 12. The chamber 4 is in fluid communication with an air inlet 14 formed in the aerosol-generating device 2 and an air outlet 16 in the mouthpiece 8 when the device 2 is assembled. Air is drawn through the device by application of negative pressure, which is usually created by a user drawing air from the air outlet.

Figure 3:
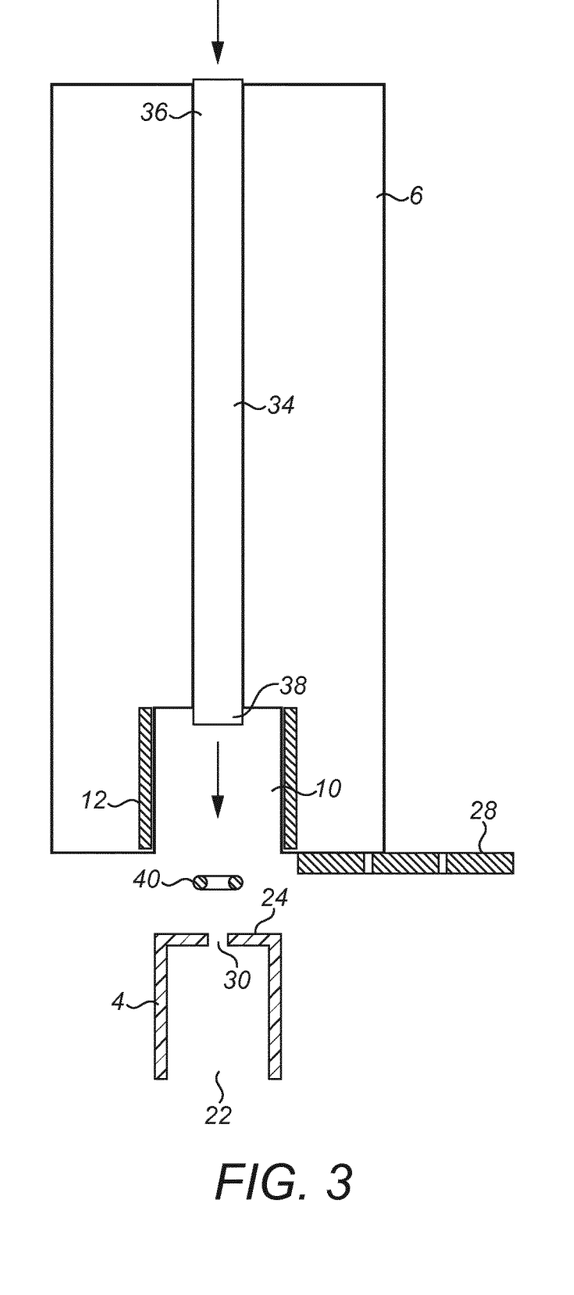
FIG. 3 is a schematic view of an aerosol-generating device comprising a removable chamber.
Figure 4:
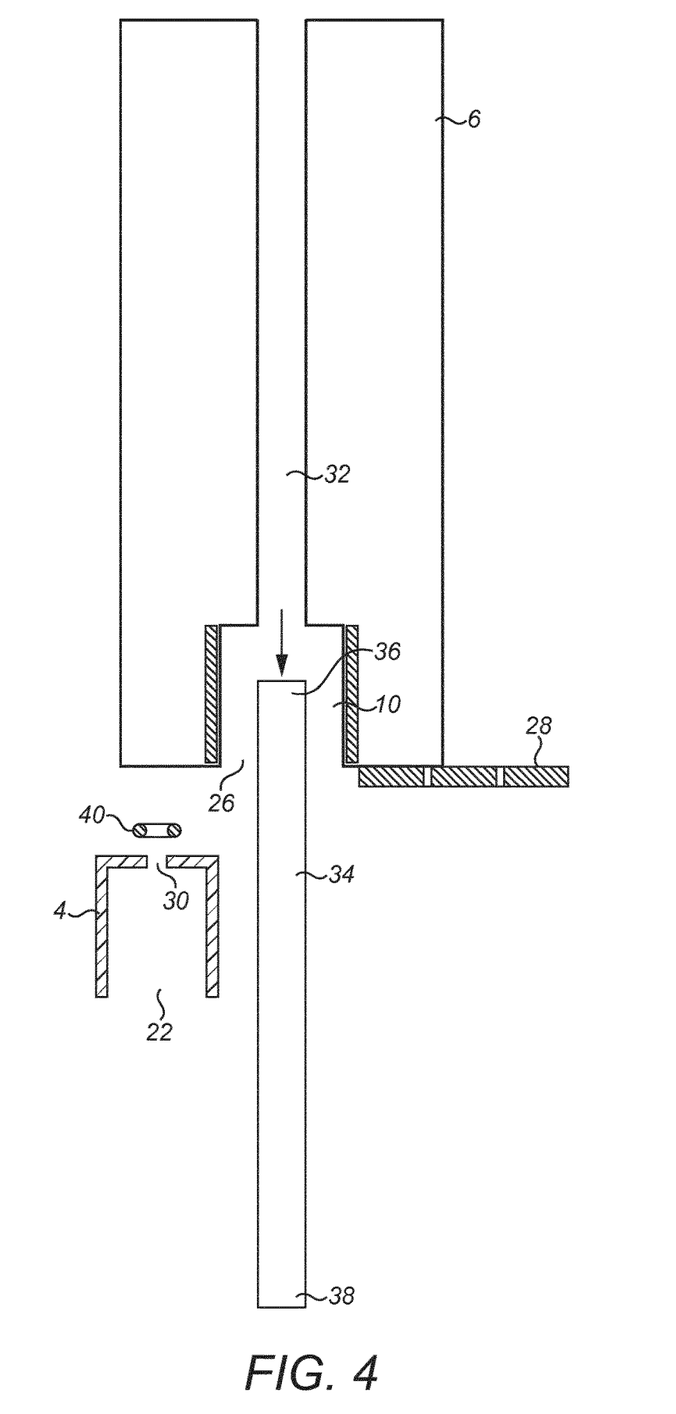
FIG. 4 is a schematic view of an aerosol-generating device comprising a removable chamber.
Figure 5:
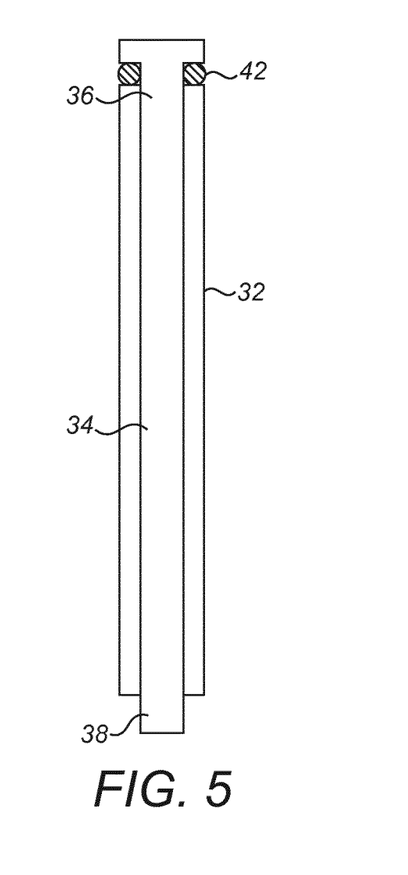
FIG. 5 is a schematic view of an alternative fluid passageway in an aerosol-generating device.
Figure 6:
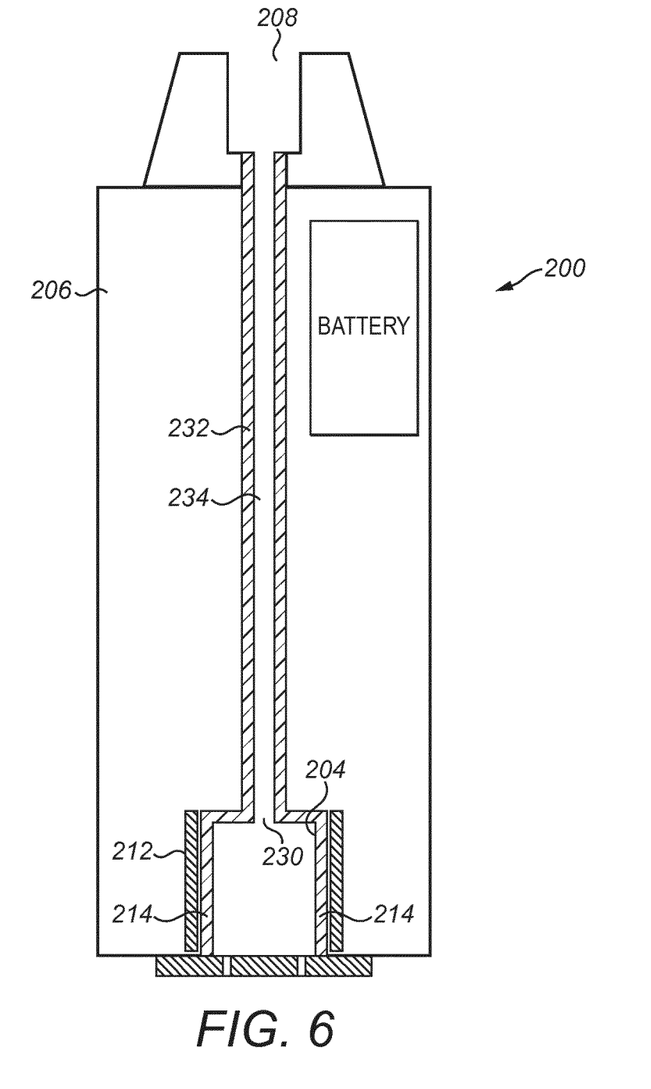
FIG. 6 is a schematic view of an alternative aerosol-generating device comprising a removable chamber.

The aerosol-generating unit 6 comprises a generally cylindrical-shaped body having a first end 18 and a second end 20. The first end 18 is substantially opposite the second 20 of the unit 6. The heating portion 10 is located at the first end 18 of the unit 6, which can be seen more clearly in FIG. 3.

The heating portion 10 is substantially surrounded by the heater 12. The heater 12 is a resistive heater, however any other suitable form of heating mechanism could be used instead.

The heating portion 10 in the unit 6 defines an opening 26 in the unit 6 so that the heating portion 10 can receive the heating chamber 4 through the opening 26. The heating portion 10 is therefore shaped to correspond to the shape of the heating chamber 4. In particular, the internal surface of the heating portion 10 substantially corresponds to the external surface of the heating chamber 4. There is therefore a tight fit between the heating portion 10 and the chamber 4. As a result, the chamber 4 is held in place through friction. The chamber 4 is therefore prevented from becoming dislodged or moving around inside the heating portion 10 while the aerosol-generating device 2 is in use.

The heating chamber 4 is generally cylindrical in shape, having a first end 22 and a second end 24. The first end 22 is open-ended and the second end 24 is closed. Thus, the chamber 4 is substantially cup-shaped.

When the chamber 4 has been inserted into the heating portion 10 of the aerosol-generating unit 6, the open end 22 of the chamber 4 coincides with the opening 26 in the aerosol-generating unit 6, defined by the heating portion 10.

As mentioned, the chamber 4 is for receiving an aerosol-generating substance. The user places the aerosol-generating substance into the chamber 4 through the opening 26 in the aerosol-generating unit 6.

To ensure that the aerosol-generating substance does not fall out of the chamber 4, the opening 26 in the aerosol-generating unit 6 is sealed by a cover 28. The cover therefore acts as a lid. The cover 28 also ensures that the aerosol-generating substance is sealed from the surrounding environment to ensure efficient generation of the aerosol from the aerosol-generating substance.

The lid 28 is attached to an external surface of the aerosol-generating unit 6 at the first end 18 of the aerosol-generating unit 6. In this example, the lid 28 is attached to the aerosol-generating unit 6 using a slide mechanism. The first end of the aerosol-generating unit 6 comprises a rail on which a corresponding runner on the lid 28 is configured to slide. The user pushes the lid 28 along the rail, away from the opening 26, to open or unseal the aerosol-generating unit 6 and the chamber 4. To close, or re-seal, the aerosol-generating unit 6 and chamber 4, the user pushes the lid 28 back along the rail towards the opening 26 until the opening 28 is completely covered. The lid 28 is held in place by a releasable locking mechanism to prevent the lid 28 from sliding open when the aerosol-generating device 2 is being used. As will be appreciated, the slide mechanism could comprise more than one rail. As will be appreciated, although the lid has been described as being attached using as slide mechanism, in some examples a pivotable joint, such as a hinge joint, may be used instead.

In this example, air inlets 14 are located in the lid 28 so that when the chamber 4 is sealed, the user is able to draw air into the chamber 4 and through the aerosol-generating unit 6 towards the mouthpiece 8. The chamber 4 is therefore in fluid communication with the atmosphere when the lid 28 is closed through the provision of the air inlets 14.

In another example, the air inlets 14 are located within the body of the aerosol-generating unit 6, between the lid 28 and the chamber 4. In this case, the air inlets 14 are provided as grooves which extend away from the heating portion 10, towards the external surface of the aerosol-generating unit 6. Thus, when the lid 28 is closed, air is still able to be drawn into the chamber 4 through the air inlets 14.

Thus, in both examples, when the lid 28 is closed the chamber 4 remains in fluid communication with the atmosphere to allow air to be drawn into the chamber through the air inlets 14.

The closed end 24 of the chamber 4 includes a small opening 30. The opening 30 is located substantially centrally within the closed end 24 of the chamber 4. The opening 30 in the chamber 4 allows the generated aerosol to exit the chamber 4. The width of the opening 30 is less than the overall width of the chamber 4. For example, a cylindrical chamber 4 would have a closed end 24 whose opening 30 has a diameter which is less than the diameter of the chamber 4. As can be seen for example in FIG. 3, the opening 30 in the chamber 4 is substantially less than the total width of the closed end 24 of the chamber 4. This provides a controlled exit for the aerosol to leave the chamber 4 and concentrates the aerosol into a stream to be inhaled by the user.

The chamber opening 30 is in fluid communication with the mouthpiece 8, providing a pathway for the user to inhale the aerosol generated in the chamber 4. A fluid passageway 32, which acts as a vapour passage, connects the chamber opening 30 to the mouthpiece 8. The fluid passageway 32 is located substantially central to the aerosol-generating unit 6 and is substantially in line with the longitudinal axis of the aerosol-generating unit 6. The fluid passageway 32 is substantially straight, providing the shortest path between the chamber 4 and mouthpiece 8. A straight passageway 32 also reduces the chance of aerosol condensing on the internal walls of the fluid passageway 32 at bends or curves in the passageway 32.

Located within the passageway is fluid tube 34. The fluid tube may also be referred to as a vapour tube. The tube 34 provides the fluid connection between the chamber 4 and the mouthpiece 8. Aerosol generated in the chamber 4 is able to flow along the tube 34 from the chamber 4 to the air outlet 16 in the mouthpiece 8.

The fluid tube 34 has a length that is greater than the length of the fluid passageway 32. Thus, when the tube 34 is located within the passageway 32, an end 36 of the tube 34 protrudes out and away from the passageway 32. The protruding end 36 extends into the mouthpiece 8, as can be seen in, for example, FIG. 1. Providing a protruding tube 34 ensures complete transfer of the aerosol into the mouthpiece 8 for inhalation by the user.

The fluid tube 34 is arranged to be inserted into and removed from the fluid passageway 32 through the opening 26 in the aerosol-generating unit 6. Thus, the fluid tube 34 and the chamber 4 are both inserted into the aerosol-generating unit 6 via the same opening 26, which keeps the structure of the device 2 simple and ensures all the components of the aerosol-generating device 2 are lined-up correctly with each to help with the flow of the aerosol within the aerosol-generating unit 6.

In order to prevent the tube 34 from slipping out of the aerosol-generating unit 6 or becoming dislodged, there is a snug fit between the external surface of the fluid tube 34 and the internal surface of the fluid passageway 32. The fluid tube 34 is therefore held in place by friction. The friction fit also prevents the tube 34 from falling out the opening 26 when the chamber 4 has been removed from the aerosol-generating unit 6.

Between the other end 38 of the tube 34 and the chamber 4 is a sealing means 40 for sealing the join between the chamber 4 and the fluid tube 34 in the fluid passageway 32. The sealing means 40 is an O-ring, as shown in FIGS. 1 and 2. The sealing means 40 keeps the aerosol-generating unit 6 fluid tight and ensures that the aerosol is contained within the aerosol-generating unit 6.

The sealing means 40 is able to be removed from the aerosol-generating unit 6 in order to allow the fluid tube 34 to be removed from the fluid passageway 32.

The mouthpiece 8 is also able to be detached from the aerosol-generating unit 6. The mouthpiece 8 is attached to the aerosol-generating unit 6 using a releasable attachment means, for example a screw mechanism. When the mouthpiece 8 is attached to the aerosol-generating unit 6, the fluid tube 32 is in fluid communication with the air outlet 16 in the mouthpiece 8. When the mouthpiece 8 is detached from the aerosol-generating unit 6, the protruding end 36 of the fluid tube 34 is exposed and accessible by the user.

In order to remove the chamber 4 from the aerosol-generating unit 6, the user first removes the cover 28 from the first end 18 of the aerosol-generating unit 6 to unseal the opening 26 in the aerosol-generating unit 6. This exposes the chamber 4 through the opening 26 and provides a clear pathway for the chamber 4 to leave the heating portion 10, as shown in FIG. 2.

The user then removes the mouthpiece 8 from the second end 20 of the aerosol-generating unit 6, for example by unscrewing the mouthpiece 8. This exposes the end 36 of the fluid tube 34 which protrudes from the aerosol-generating unit 6, as shown in FIG. 3.

To remove the chamber 4, the user then pushes on the exposed end 36 of the fluid tube 34. The exposed end 36 of the tube 34 is pushed towards the main body of the aerosol-generating unit 6 until the end 36 of the fluid tube 34 is flush with the end 20 of the aerosol-generating unit 6. By pushing on the end 36 of the fluid tube 34, the tube 34 is forced through the fluid passageway 32 and presses on the sealing means 40 which, in turn, presses on the closed end 24 of the chamber 4. The fluid tube 34 dislodges the seal 40 and the chamber 4 so that they can both be removed through the opening 26 in the aerosol-generating unit 6.

The user can then take hold of the first end 38 of the fluid tube 34, which is now exposed inside the heating portion 10, and pull the fluid tube 34 out of the fluid passageway 32 through the opening 26 in the aerosol-generating unit 6, as shown in FIG. 4. The user can then clean the fluid tube 24 and the heating chamber 4.

To reassemble the device 2, the user first inserts the fluid tube 34 into the fluid passageway 32 via the opening 26 in the aerosol-generating unit 6. The user pushes the fluid tube 34 completely into the fluid passageway 32, until the second end 36 of the tube 34 protrudes from the mouthpiece-end 20 of the aerosol-generating unit 6. The user then inserts the seal 40 followed by the chamber 4 through the same opening 26.

Once the seal 40 and chamber 4 are in place, the user can re-seal the opening 26 by closing the lid 28. The user can also re-attach the mouthpiece 8 to the other end 20 of the aerosol-generating unit 6. The aerosol-generating device 2 is then fully re-assembled and is ready to be used.

In other examples, a second sealing means 42 is provided at the protruding end 36 of the fluid tube 34, as can be seen in FIG. 5. The second sealing means 42 is another O-ring and seals the join between the fluid passageway 32, fluid tube 34, and the mouthpiece 8.

FIG. 6 shows an alternative embodiment of a portable aerosol-generating device 200. In a similar manner to before, heating is achieved by the chamber 204 being surrounded by a heating element, or heater, 212. In some embodiments, the heating element 212 is a flexible sheet type heating element. The walls of the chamber 204 are made of stainless steel. The stainless steel effectively conducts heat from the heating element 212 to the chamber 204 to heat the aerosol-generating substance inside the chamber 204.

As before, the chamber 204 comprises an opening 230 in fluid communication with the mouthpiece 208 via a fluid passageway 232. A fluid tube portion 234, which connects the chamber opening 230 to the mouthpiece 208 and is located inside the fluid passageway 232, is integrally formed with the chamber 204, as can be seen in FIG. 6 That is, the fluid tube 234 and chamber 204 form a combined chamber and air flow tube unit 214. This unit 214 is arranged to be inserted into and removed from the fluid passageway 232 in the aerosol-generating unit 206 in a similar manner as before. The aerosol-generating device 200 of this embodiment therefore comprises fewer individual components, making the device easier to assemble and disassemble. A single chamber and air flow tube unit 214 also provides a robust fluid tight connection between the chamber 204 and the fluid tube 234. This ensures that substantially all the aerosol generated in the chamber 204 can be inhaled by the user through the mouthpiece 208.

In addition, the likelihood of any aerosol leaking into the aerosol-generating device 200 is greatly reduced.

The fluid tube portion 234 of the air flow tube unit 214 is made of a material having a lower heat conductivity than the material from which the chamber 204 is made. A thermal break is therefore introduced into the unit 214 at the place where the chamber 204 and fluid tube portion 234 are joined together. The thermal break prevents or reduces heat from the chamber 204 from being transferred up the fluid tube portion 234. This ensures that the temperature inside the fluid tube portion 234 is cooler than the temperature inside the chamber 204. This helps to effectively cool down the aerosol.

The invention claimed is:

1. A portable aerosol-generating device for receiving an aerosol-generating substance, the device comprising:
   a chamber arranged to receive an aerosol-generating substance, the chamber configured to be connected to a mouthpiece via a fluid passageway;
   an aerosol-generating unit configured to generate an aerosol from the aerosol-generating substance for a user to inhale in use; and
   a fluid tube configured to be releasably inserted into the fluid passageway,
   wherein the chamber is configured to be releasably inserted into the device through an opening in the device, and
   wherein an end of the fluid tube is configured to dislodge the chamber.

2. The device according to claim 1, wherein the opening is arranged in the aerosol-generating unit and the chamber is configured to be releasably inserted into the aerosol-generating unit through the opening.

3. The device according to claim 1, wherein the opening is configured to be closed.

4. The device according to claim 1, wherein the chamber is configured to receive the aerosol-generating substance through the opening.

5. The device according to claim 1, wherein the chamber comprises an opening.

6. The device of claim 1, wherein the fluid tube is configured to be releasably inserted into the fluid passageway through the opening in the aerosol-generating device.

7. The device according to claim 1, wherein a length of the fluid tube is greater than a length of the fluid passageway.

8. The device according to claim 1, further comprising at least one sealing means to seal between the end of the fluid tube and the fluid passage, or, between the end of the fluid tube and the chamber.

9. The device according to claim 1, wherein the chamber is configured to be removed from the aerosol-generating device by using the fluid tube to dislodge the chamber through the opening in the device.

10. The device according to claim 1, wherein the fluid tube comprises a low heat conductive material whose heat conductivity is less than a conductivity of a material from which the chamber is made.

11. The device according to claim 1, further comprising an induction heater having an electromagnetic inductor surrounding or positioned next to the chamber.

12. The device according to claim 11, wherein the chamber comprises a susceptor.

13. The device of claim 1, further comprising the mouthpiece.

14. A method of releasably inserting a chamber into an aerosol-generating device, the method comprising the steps of:
    providing an aerosol-generating device comprising an opening;
    releasably inserting the chamber through the opening in the device, wherein the chamber is configured to receive an aerosol-generating substance into the aerosol-generating device; and
    releasably inserting a fluid tube into a fluid passageway, wherein the fluid passageway is configured to connect the chamber with a mouthpiece, wherein the end of the fluid tube is configured to dislodge the chamber.

* * * * *